(12) United States Patent
Favre et al.

(10) Patent No.: US 8,273,359 B2
(45) Date of Patent: Sep. 25, 2012

(54) THERAPEUTIC USE OF AT LEAST ONE BOTULINUM NEUROTOXIN IN THE TREATMENT OF PAIN INDUCED BY AT LEAST ONE ANTI-NEOPLASTIC AGENT

(75) Inventors: Christine Favre, Saint Maurice Montcouronne (FR); Michel Auguet, Palaiseau (FR); Pierre-Etienne Chabrier De Lassauniere, Paris (FR)

(73) Assignee: Ipsen Pharma S.A.S., Boulogne Billancourt (FR)

( * ) Notice: Subject to any disclaimer, the term of this patent is extended or adjusted under 35 U.S.C. 154(b) by 604 days.

(21) Appl. No.: 12/447,443

(22) PCT Filed: Oct. 26, 2007

(86) PCT No.: PCT/FR2007/001773
§ 371 (c)(1),
(2), (4) Date: Apr. 27, 2009

(87) PCT Pub. No.: WO2008/059126
PCT Pub. Date: May 22, 2008

(65) Prior Publication Data
US 2010/0068231 A1    Mar. 18, 2010

(30) Foreign Application Priority Data

Oct. 27, 2006 (FR) ..................... 06 09435

(51) Int. Cl.
*A61K 39/08* (2006.01)
*A61K 39/02* (2006.01)
*A61K 9/16* (2006.01)

(52) U.S. Cl. ............... 424/239.1; 424/247.1; 424/236.1; 424/493

(58) Field of Classification Search ........................ None
See application file for complete search history.

(56) References Cited

U.S. PATENT DOCUMENTS

| | | | |
|---|---|---|---|
| 6,368,605 B1 * | 4/2002 | Donovan ................. | 424/239.1 |
| 7,704,524 B2 | 4/2010 | Donovan | |
| 2002/0064536 A1 | 5/2002 | Hunt | |
| 2002/0192239 A1 | 12/2002 | Borodic et al. | |
| 2003/0138437 A1 | 7/2003 | Hunt | |
| 2004/0247623 A1 | 12/2004 | Cady | |
| 2005/0147625 A1 | 7/2005 | First | |
| 2005/0152905 A1 * | 7/2005 | Omoigui ................. | 424/145.1 |
| 2006/0178354 A1 | 8/2006 | Lucas | |
| 2006/0240043 A1 * | 10/2006 | Meyerson et al. ......... | 424/239.1 |
| 2006/0269575 A1 * | 11/2006 | Hunt ................. | 424/239.1 |
| 2008/0232851 A1 * | 9/2008 | Park et al. ................ | 399/159 |
| 2009/0214466 A1 * | 8/2009 | Levin ................. | 424/85.2 |
| 2009/0232849 A1 * | 9/2009 | Gallez et al. ............. | 424/239.1 |
| 2010/0029566 A1 * | 2/2010 | Favre et al. ................ | 514/12 |
| 2010/0068231 A1 * | 3/2010 | Favre et al. .............. | 424/239.1 |
| 2011/0038893 A1 * | 2/2011 | Favre et al. .............. | 424/239.1 |

FOREIGN PATENT DOCUMENTS

| | | |
|---|---|---|
| GB | 2 416 692 | 2/2006 |
| GB | 2 419 526 | 3/2006 |
| KR | 2003018827 | 3/2003 |
| WO | WO 95/17904 | 7/1995 |
| WO | WO 01/26736 A2 | 4/2001 |
| WO | WO 01/58472 | 8/2001 |
| WO | WO 01/78760 A2 | 10/2001 |
| WO | WO 2004/006954 | 1/2004 |
| WO | WO 2006/005912 | 1/2006 |
| WO | WO 2007/144493 | 12/2007 |

OTHER PUBLICATIONS

Database WPI Online, Derwent Publications Ltd., London, GB, DW: 200377, XP002439047, Database accession No. AN: 2003-826007 & KR-A-2003018827 (SEO K I) Mar. 6, 2003.
Guokai et al., Chinese Journal of Anesthesiology, vol. 23, No. 2, pp. 157-159 (2003).
Ansiaux et al. (2007) Expert Opinion on Investigational Drugs. 16(2): 209-218.
Argoff et al. (2002) The Journal of Clinical Pain. 18: S177-S181.
Attal et al. (2008) Neurology. 70(11): A167.
Auguet et al. (2008) Toxicon. 51(Suppl. 1): 9.
Blersch et al. (2002) Journal of the Neurological Sciences. 205m(1): 59-63.
Dieleman et al. (2002) Archives of Internal Medicine. 162(13): 1492-1501.
Favre-Guilmard et al. (2008) Toxicon. 51(Supp. 1): 10.
Frich et al. (2000) Journal of Pain and Symptom Management. 19(5): 339-347.
Gordon, D. (Dec. 2004) Pain Management Nursing, W.B. Saunders. 5: 19-33.
Jabbari et al. (2003) Pain Medicine. 4(2): 206-210.
Jacobson et al. (2008) Applied and Environmental Microbiology. 74(9): 2778-2786.
Joseph et al. (2004) Pain. 107: 147-158.
Kern, U., et al. (Apr. 2004) Nervenarzt, 75(4).
Keswani et al. (2002) AIDS. 16: 2105-2117.
Klein et al. (2004) Dermatologic Surgery. 30(3): 452-455.
Liu et al. (2006) Pain Medicine. 7(1): 89-91.
Lo Nigro et al. (2002) Medical and Pediatric Oncology. 38(2): 150.
Luciano et al. (2003) Current Opinion in Neurology. 16: 403-409.
Noguera et al. (2004) AIDS. 18(2): 352-353.
Park et al. (2008) Biosciences Information Service, Database Accession No. PREV200800185978.
Ranoux et al. (2008) Annals of Neurology. 64(3): 274-283.
Voller et al. (2003) Neurology. 61(7): 940-944.
Yuan et al. (2009) Neurology. 72(17): 1473-1478.
International Search Report for International Application No. PCT/FR2007/000956, mailed on Feb. 22, 2008.
International Search Report for International Application No. PCT/IB2009/005750, mailed Jul. 10, 2009.
International Search Report for International Application No. PCT/FR2007/002091, mailed Jul. 29, 2008.

(Continued)

*Primary Examiner* — Nita M Minnifield
(74) *Attorney, Agent, or Firm* — Hunton & Williams LLP

(57) ABSTRACT

The present invention relates to a method of treating or preventing pain or pains induced by an anti-neoplastic agent, comprising the step of administering an effective amount of at least one botulinum neurotoxin to a patient in need thereof.

16 Claims, 3 Drawing Sheets

OTHER PUBLICATIONS

International Search Report for International Application No. PCT/FR2007/001773, mailed Apr. 28, 2008.
Aoki, K.R., NeuroToxicology, vol. 26, pp. 785-793, (2005).
Bach-Rojecky. L. et al., Basic Science—Croatian Medical Journal, vol. 46, No. 2, pp. 201-208, (2005).
Bach-Rojecky. L. et al., Journal of Neural Transmission, vol. 112, pp. 215-219, (2005).
Cata, P. et al., Brain Research (final), National Institutes of Health, vol. 1229, pp. 100-110, Sep. 10, 2008.
Cui, M. et al., Pain, vol. 107, pp. 125-133, (2004).
Farve-Guilmard, C. et al., European Journal of Pharmacology, vol. 617, pp. 48-53, (2009).
Ledeboer, A. et al., Brain, Behavior and Immunity, Available online at www.sciencedirect.com, vol. 21, pp. 686-698, (2007).
Luvisetto, S. et al., Brain Research—Research Report, Available online at www.sciencedirect.com, Accepted Jan. 28, 2006.
Luvisetto, S. et al., NeuroScience, vol. 145, pp. 1-4, (2007).
Park, H.J. et al., Canadian Journal of Anesthesia, vol. 53, No. 5, pp. 470-477, (2006).
Polomano, R. et al., Pain, vol. 94, pp. 293-304, (2001).
Bueschen (1990) *Clinical Methods: The History, Physical, and Laboratory Examinations* [3$^{rd}$ Ed.] Chapter 182 "Flank Pain".
Dougherty, et al. (2004) *Pain* 109: 132-142.
Park & Moon (2008) "Antinociceptive Effects of Botulinum Toxin A for the Treatment of Neuropathic Pain." *Reviews in Analgesia* 10(1): 1-9 [Abstract only].
Webb, et al. (2006) *Drug Metab Rev.* 38(1-2): 89-116.
The Merck Index: An Encyclopedia of Chemicals and Drugs, 9th Ed., Merck & Co. (1976) p. 814.

* cited by examiner

THERAPEUTIC USE OF AT LEAST ONE BOTULINUM NEUROTOXIN IN THE TREATMENT OF PAIN INDUCED BY AT LEAST ONE ANTI-NEOPLASTIC AGENT

CROSS-REFERENCE TO RELATED APPLICATIONS

This application claims the benefit of and is the U.S. National Stage of International Application No. PCT/FR2007/001773 (WO 2008/059126) filed on Oct. 26, 2007, which claims the benefit of Application No. FR 0609435, filed in France on Oct. 27, 2006. The contents of these disclosures are hereby incorporated by reference thereto.

FIELD OF THE INVENTION

A subject of the present invention is the use of at least one botulinum neurotoxin for obtaining a medicament intended to treat or prevent post-chemotherapy pain or pains associated with an antineoplastic treatment.

BACKGROUND

Post-chemotherapy neuropathy, which is a pain caused by a chemical treatment for combating cancer, still remains today a pathology which is difficult to relieve or cure. This type of pain is to be distinguished from pain caused by cancerous tumours themselves. In fact post-chemotherapy neuropathy is induced by the anti-neoplastic agent administered to the patients for treatment purposes.

Post-chemotherapy neuropathic pains have particular semiological characteristics. Generally, these pains are characterized inter alia by a continuous, diffuse pain, without mechanical or inflammatory pattern, of burning type. Against this background of continuous pain, other symptoms can occur: spontaneous attacks of the shooting-pain type, tingling, more particularly tingling at limb extremities, or also electric discharges. The topography of these symptoms corresponds to a distribution compatible with a peripheral or central systematization. In other words the topography of these post-chemotherapy neuropathic pains is independent of the topography of the cancerous tumours.

Among the known treatments for this pain, there may be mentioned the administration of anticonvulsants, antidepressants or opiate compounds such as morphine, which was isolated right at the start of the 19th century by a German pharmacist, Friedrich Sertürner, from the opium of which it is the main constituent.

Moreover the World Health Organization recommends three levels of prescription for analgesic medicaments, a rule which proves effective in 70% of patients:

Level I: non-opioid analgesics for mild to moderate pains
Level II: weak opioid analgesics combined with non-opioids for moderate to intense pains.
Level III: strong opioid analgesics for intense to very intense pains.

However the use of the compounds currently available which make it possible to reduce pain caused by an antineoplastic treatment is not satisfactory as it requires the use of high doses of compounds, or frequent re-administration of the compound with possible development of a resistance to the compound or habituation. Moreover these anti-pain treatments can cause side effects, which are added to those already caused by the cancer.

It has therefore become necessary to find another means for treating these post-chemotherapy neuropathic pains.

Thus the problem that the invention proposes to solve is to find a novel treatment for the pain caused by treatment with an antineoplastic agent.

SUMMARY OF THE INVENTION

Unexpectedly, the inventors have demonstrated that the administration of botulinum neurotoxin has an analgesic effect in the treatment of pain caused by chemotherapy.

To this end the present invention proposes the use of at least one botulinum neurotoxin for obtaining a medicament intended to treat or prevent post-chemotherapy pain or pains.

The invention offers decisive advantages, in particular that of avoiding or preventing pain following a treatment with an anti-neoplastic agent and thus allowing the treatment doses to be increased without increasing the pain.

Finally an advantage of the invention is that it can be implemented in all industries, in particular the pharmaceutical, veterinary and cosmetic industries.

Other advantages and characteristics of the invention will become clearly apparent on reading the following description and examples which are given purely by way of illustration and are not limitative.

By "pain" within the meaning of the present invention is meant "any unpleasant emotional and sensory experience associated with present or potential tissue damage or described in such terms by the patient".

By the expression botulinum neurotoxin, is meant a botulinum toxin which is either a free protein (i.e. free of any protein complexing it), or a protein complex, said protein complex being able to comprise for example hemagglutinin (HA protein) combined with the botulinum toxin, or a protein fragment.

By the expression botulinum toxin, is meant a molecule possessing the biological activity of the botulinum toxin, which can be for example either a protein, or a polypeptide, or a peptide, or a fusion protein, or a truncated protein, or a chimeric protein, or a mutated protein or a recombinant protein.

By the expression biological activity of the botulinum toxin, is meant within the meaning of the present invention either muscle paralysis or inhibition of exocytosis, in particular acetylcholine exocytosis or exocytosis of another neurotransmitter.

By protein, polypeptide or peptide is meant within the meaning of the present invention, a polymer of amino acids, natural or non-natural, levogyratory or non-levogyratory, dextrogyratory or non-dextrogyratory.

By chimeric protein, is meant within the meaning of the present invention a protein obtained after combination of different types of molecules, for example after combination of lipids, glycolipids, peptides, polypeptides, proteins, glycoproteins, carbohydrates, polysaccharides, nucleic acids, polyethylene glycol, etc.

Botulinum toxin, in particular botulinum toxin type A1 (Dysport® (abobotulinumtoxinA) marketed by Ipsen or Botox® (onabotulinumtoxinA) marketed by Allergen), has been used in humans for the treatment of many and varied diseases/disorders since the 1980s. Among the diseases/disorders which can be treated with botulinum toxin, there may be mentioned, amongst others, muscular disorders (for example blepharospasm, adult or child spasticity or also torticollis), migraine, pain of muscular origin, diabetes, hyperhidrosis (or excessive perspiration), hypersalivation or even wrinkles.

The botulinum neurotoxin, pure or virtually pure, can be obtained from a protein complex comprising botulinum toxin for example according to the method described in *Current topics in Microbiology and Immunology* (1995), 195, p. 151-154. A botulinum neurotoxin, pure or virtually pure, can be obtained for example, by purification of a fermentation medium or culture medium containing a strain of *Clostridium Botulinum*, and enriched for example with meat or protein-rich food.

DETAILED DESCRIPTION

Figure 1:
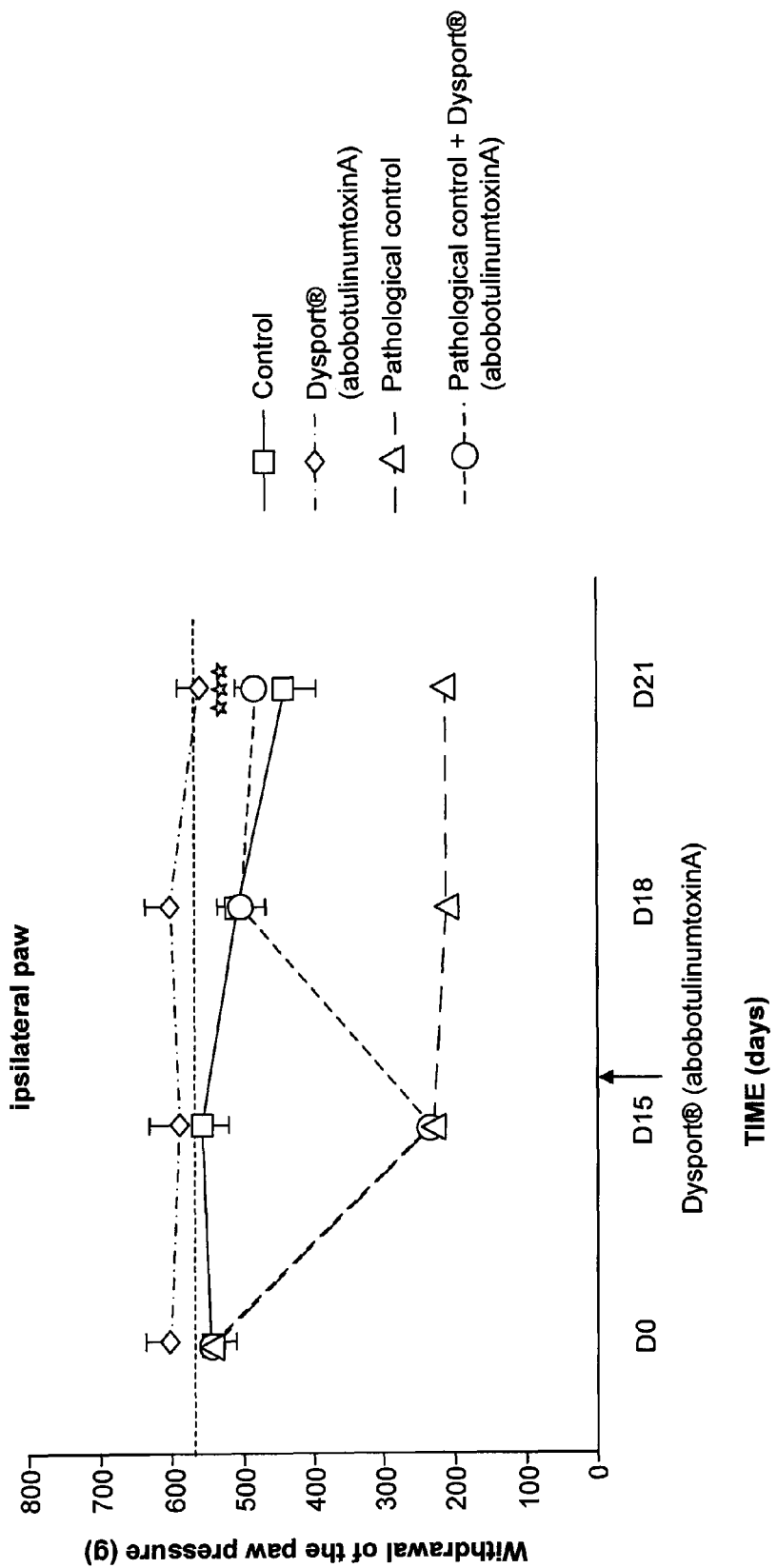
FIG. 1 shows the effect of botulinum toxin type A1 on the right paw following the injection by subplantar route into the right paw (ipsilateral) in the model of peripheral neuropathy induced by paclitaxel.

A subject of the present invention is firstly the use of at least one botulinum neurotoxin for obtaining a medicament intended to treat or prevent post-chemotherapy pain or pains.

More particularly, a subject of the present invention is the use of at least one botulinum neurotoxin for obtaining a medicament intended to treat or prevent post-chemotherapy pain or pains it being understood that the botulinum neurotoxin is administered by localized route making it possible to obtain a generalized effect.

Preferably, the subject of the present invention is not to treat cancers, nor tumours, nor pains induced by tumours, in particular pains associated with bone tumours.

Preferably, the use according to the invention of at least one botulinum neurotoxin for obtaining a medicament makes it possible to treat or prevent post-chemotherapy pains induced by an anti-neoplastic agent or its salts or its derivatives.

Preferably, the anti-neoplastic agent or its salts or its derivatives are chosen from the following compounds or their mixtures: taxanes, platinum salts, or other antineoplastic agents.

Preferably, the anti-neoplastic agent or its salts or its derivatives are chosen from taxanes such as for example docetaxel, paclitaxel TAXOL® or their mixtures.

Preferably, the anti-neoplastic agent or its salts or its derivatives are chosen from platinum salts such as for example cisplatin, oxaliplatin or carboplatin or their mixtures.

Preferably, the anti-neoplastic agent or its salts or its derivatives are chosen from vincristine, vinblastine, etoposide, teniposide, Ara-A (adenoside-arabinoside), Ara-C (cytarabine), fluorouracil, procarbazine, vinorelbine, gemcitabine, or also products or mixtures of products such as paclitaxel/carboplatin, paclitaxel/anthracyclines, paclitaxel/carboplatin/gemcitabine, paclitaxel/estramustine, docetaxel/cisplatin, docetaxel/doxorubicin, docetaxel/vinorelbine, docetaxel/trastuzumab, docetaxel/capecitabine or cisplatin/cyclophosphamide, cisplatin/irinotecan, carboplatin/topotecan, carboplatin/estramustine, etoposide/estramustine, vinblastine/estramustine.

By salt is meant a pharmaceutically acceptable salt and in particular addition salts with inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate.

Also included within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

Preferentially, the botulinum neurotoxin makes it possible to obtain a systemic effect.

By "systemic effect", is meant within the meaning of the present invention a localized administration making it possible to obtain a generalized effect.

According to a preferred use of the invention, the botulinum neurotoxin is administered by intramuscular, intradermal, or subcutaneous route.

Preferably, the botulinum toxin used according to the invention is chosen from the botulinum toxins of type A, A1, A2, B, C, C1, D, E, F or G.

The botulinum neurotoxin type A1 corresponds in fact to the standard botulinum toxin which is commonly called botulinum toxin type A, irrespective of the subtype. Botulinum neurotoxin type A1 is marketed under the name of DYSPORT® (abobotulinumtoxinA) or BOTOX® (onabotulinumtoxinA).

According to the invention, the botulinum neurotoxin type A1 can correspond either to a complex of botulinum toxin A1 and hemagglutinin, or to botulinum toxin type A1 free of all complexing proteins.

The botulinum toxin type A2 was first isolated from cases of children suffering from botulism around 1990 (Sakaguchi et al., *Int. J. Food Microbiol.* (1990), 11, 231-242). This toxin is immunologically and biochemically different from botulinum toxin type A1.

The botulinum toxin type A2 can be isolated from the following strains: Kyoto-F, Chiba-H, Y-8036, 7103-H, 7105-H, KZ1828, NCTC2012 or NCTC9837 (Cordoba et al., *System. Appl. Microbiol.* (1995), 18, 13-22; Franciosa et al., abstract presented at $40^{th}$ Interagency Botulism Research Coordinating Committee (IBRCC) Meeting, November 2003).

Preferably the botulinum toxin used according to the invention is botulinum toxin type A1.

According to a variant of the invention, the botulinum neurotoxin used according to the invention is botulinum toxin type A2 isolated from the strain *Clostridium botulinum* referenced and accessible under number NCTC9837, at the National Collection of Type Cultures—Central Public Health Laboratory—London—UK. The strain NCTC9837 is sometimes called Mauritius 1955 strain.

Botulinum toxin type A2 differs from toxin A1 by, inter alia, its amino acid sequence, its molecular weight, its immunological and genetic characteristics (Kubota et al., *Biochem. Biophys. Res. Commun.* (1996), 224 (3), 843-848).

According to a preferential embodiment, the botulinum neurotoxin used according to the invention is a modified botulinum neurotoxin having at least one deleted, modified or replaced amino acid.

Preferably the botulinum neurotoxin used according to the invention is combined with at least one polysaccharide or a mixture of several polysaccharides.

By polysaccharide, is meant within the meaning of the present invention a polymer comprising at least 2 monomers, the monomers being saccharides. This definition includes the disaccharides.

Within the framework of the invention, the polysaccharides can be ionic and/or non ionic.

Preferably, the composition comprises at least one polysaccharide comprising mainly glucose units. The term "mainly" means that glucose comprises the majority by number of monomer units.

As examples of suitable polysaccharides according to the use of the invention, there may be mentioned starch, starch derivatives, hydroxyethyl starch in particular 2-hydroxyethyl starch.

The suitable polysaccharides according to the present invention can be substituted, in particular they can be substituted by alkyl, alkoxy radicals, or also by alkyl radicals themselves substituted by alcohol functions.

According to a variant of the invention, the quantity of suitable polysaccharide according to the present invention is at least 1 µg of polysaccharide per unit of botulinum toxin. According to the choice of polysaccharide, it is possible to use at least 0.5 µg of polysaccharide per unit of botulinum toxin.

Preferably the botulinum neurotoxin used according to the invention is combined with at least one surfactant or a mixture of several surfactants.

By surfactant, is meant within the meaning of the invention an emulsifying agent or a solubilizing agent.

Within the framework of the invention the surfactants used can be chosen from the cationic, anionic or non-ionic surfactants.

Preferably the botulinum neurotoxin used according to the invention is combined with at least one surfactant or a mixture of several surfactants, chosen from the cationic, anionic or non-ionic surfactants.

Preferably the botulinum neurotoxin used according to the invention is combined with at least one surfactant chosen from the non-ionic surfactants of the polysorbates group.

Among the polysorbates group, there may be mentioned polysorbate 20, polysorbate 21, polysorbate 40, polysorbate 60, polysorbate 61, polysorbate 65, polysorbate 80, polysorbate 81, polysorbate 85, polysorbate 120, polysorbate 80 acetate.

The preferred surfactant according to a variant of the invention is polysorbate 80.

The botulinum neurotoxin used according to the invention can be administered preferably by injection such as for example by intramuscular, intradermal or subcutaneous injection, or also by topical application for example application of a patch.

In the case of the injections according to the invention, the botulinum neurotoxin can be combined with an agent facilitating the injection, also called an injection vehicle or an injection vector.

The dose for use of the botulinum neurotoxin according to the present invention to be provided for the treatment of the diseases or disorders mentioned above, varies depending on the administration method, the age and body weight of the subject to be treated as well as the state of the latter, and will be finally decided by the attending doctor or vet. Such a quantity determined by the attending doctor or vet is here called the "therapeutically effective quantity".

Preferably, the botulinum neurotoxin used according to the invention is administered at a dose comprised between 0.01 U and 1500 U, preferentially at a dose comprised between 0.01 U and 1000 U, more preferentially 0.1 to 500 U, more particularly at a dose comprised between 0.1 and 100 U, still more particularly at a dose comprised between 1 and 20 U, regardless of the type of botulinum toxin or its origin. (The unit of toxin (U) is defined in the experimental part).

A subject of the present invention is the use of the botulinum neurotoxin described above, for obtaining a medicament intended to treat or prevent post-chemotherapy pain or pains, i.e. pains linked to an anti-cancer treatment.

By the expression "cancer", is meant within the meaning of the invention any type of cancer, i.e. invasive, non invasive, infiltrating, hormonal, non-hormonal, localized or metastatic.

According to a preferred use of the invention, botulinum neurotoxin makes it possible to treat or prevent post-chemotherapy pain or pains in patients suffering for example from cancers of the colon, rectum, breast, lungs, pancreas, testicles, kidney, uterus, ovary, prostate, skin, bones, spinal cord as well as patients suffering from sarcomas, carcinomas, fibroadenomas, neuroblastomas, leukaemias, lymphomas, or melanomas.

The following examples illustrate the invention without limiting its scope.

EXAMPLES

Measurement of the quantity of botulinum neurotoxins used according to the invention was carried out by measuring a lethal dose $LD_{50}$. By $LD_{50}$, is meant within the meaning of the present invention the lethal dose or also semi-lethal dose of a given substance. It is the dose (or quantity) which leads to the death of 50% of the animals tested in a group. A unit of toxin (U) corresponds to the $LD_{50}$ in mice by intraperitoneal route.

Model of Neuropathy Induced by Administration of an Antineoplastic Agent.

The activity of Dysport® (botulinum toxin type A1) was evaluated in vivo on a model of peripheral neuropathy induced by administration of an antineoplastic agent: Paclitaxel (Taxol®).

Male Sprague Dawley (Charles River) rats weighing approximately 160 g are housed for 6 days under animal room conditions. 4 groups of at least 10 animals are formed.

The neuropathy is induced by intra-peritoneal (i.p.) injections of 2 mg/kg of paclitaxel on days D0, D2, D4 and D7.

Before the first injection, the rats are numbered and weighed and nociception (pain threshold) is evaluated after a mechanical stimulus the pressure of which increases: inducing an initial pressure ($210 \text{ g/mm}^2$) on the rats' two rear paws carried out using an analgesia meter according to the Randall and Selitto method. These measurements allow the base values to be defined before development of the neuropathy (D0).

The decrease in the nociceptive threshold corresponding to the neuropathic impairment is at a maximum between the 14th and the 24th day after the first injection of paclitaxel. The nociception threshold of the rats' two rear paws is decreased similarly. The neuropathy studies are thus carried out between the 14th and the 24th day on the rats' rear paws. In the case described, the nociception measurements are carried out on days D18 and D21.

On the day of the experiment (D15), the rats are weighed, nociception is measured and the animals which have not developed the neuropathy on this day (reduction of nociception in comparison with the measurements on D0) are excluded from the study. The Dysport® (abobotulinumtoxinA) is injected subplantar into the right (ipsilateral) rear paw of the rats and the nociception is measured on the 2 rear paws (ipsilateral and contralateral) 3 days and 6 days after its administration.

Effect of Dysport® (abobotulinumtoxinA) on Neuropathy Induced by Taxol:

FIG. 1 represents the effect of Dysport (abobotulinumtoxinA) on the right paw following its injection by subplantar route into the right (ipsilateral) paw in the model of peripheral neuropathy induced by paclitaxel.

The control indicates the pain threshold tolerated by the rat when increasing pressure is applied to its paws; this group was treated with the paclitaxel vehicle (3% MONTANOX® (polysorbate 80) in 0.9% NaCl) by intraperitoneal route and with the Dysport® (abobotulinumtoxinA) vehicle (0.9% NaCl) subplantar. From D0 to D21, the nociception threshold is situated at approximately 500 g/mm$^2$.

The pathological control indicates the pain threshold tolerated by the rat when increasing pressure is applied to its paws; this group was treated with paclitaxel by intraperitoneal route and with the Dysport® (abobotulinumtoxinA) vehicle (0.9% NaCl) subplantar. On day zero this threshold is approximately 544 g/mm$^2$, then decreases reaching 232 g/mm$^2$ on day 15, 216 g/mm$^2$ on day 18 and 216 g/mm$^2$ on day 21. These results indicate that after i.p. injection of paclitaxel, the sensitivity of the paws of the rats is increased following the application of pressure on them.

The administration of Dysport® (abobotulinumtoxinA) at a dose of 20 U/kg subplantar in a group treated only with the paclitaxel vehicle (3% MONTANOX® (polysorbate 80) in 0.9% NaCl) by intra-peritoneal route, indicates that the pain threshold tolerated by the rat is not significantly modified. The pain threshold following a mechanical stimulus applied to the paws of the rats is approximately 590 g/mm$^2$ from D0 to D21.

The administration of Dysport® (abobotulinumtoxinA) at a dose of 20 U/kg subplantar in a group treated with paclitaxel indicates that the pain threshold tolerated by the rat on its right paw increases. The pain threshold following a mechanical stimulus applied to the paws of the rats is significantly increased, reaching approximately 500 g/mm$^2$ on D18 (i.e., 3 days after the treatment with Dysport® (abobotulinumtoxinA)) and 480 g/mm$^2$ on D21 (i.e., 6 days after the treatment with Dysport® (abobotulinumtoxinA)) compared with 232 g/mm$^2$ on D15 (before Dysport® (abobotulinumtoxinA)).

Figure 2:
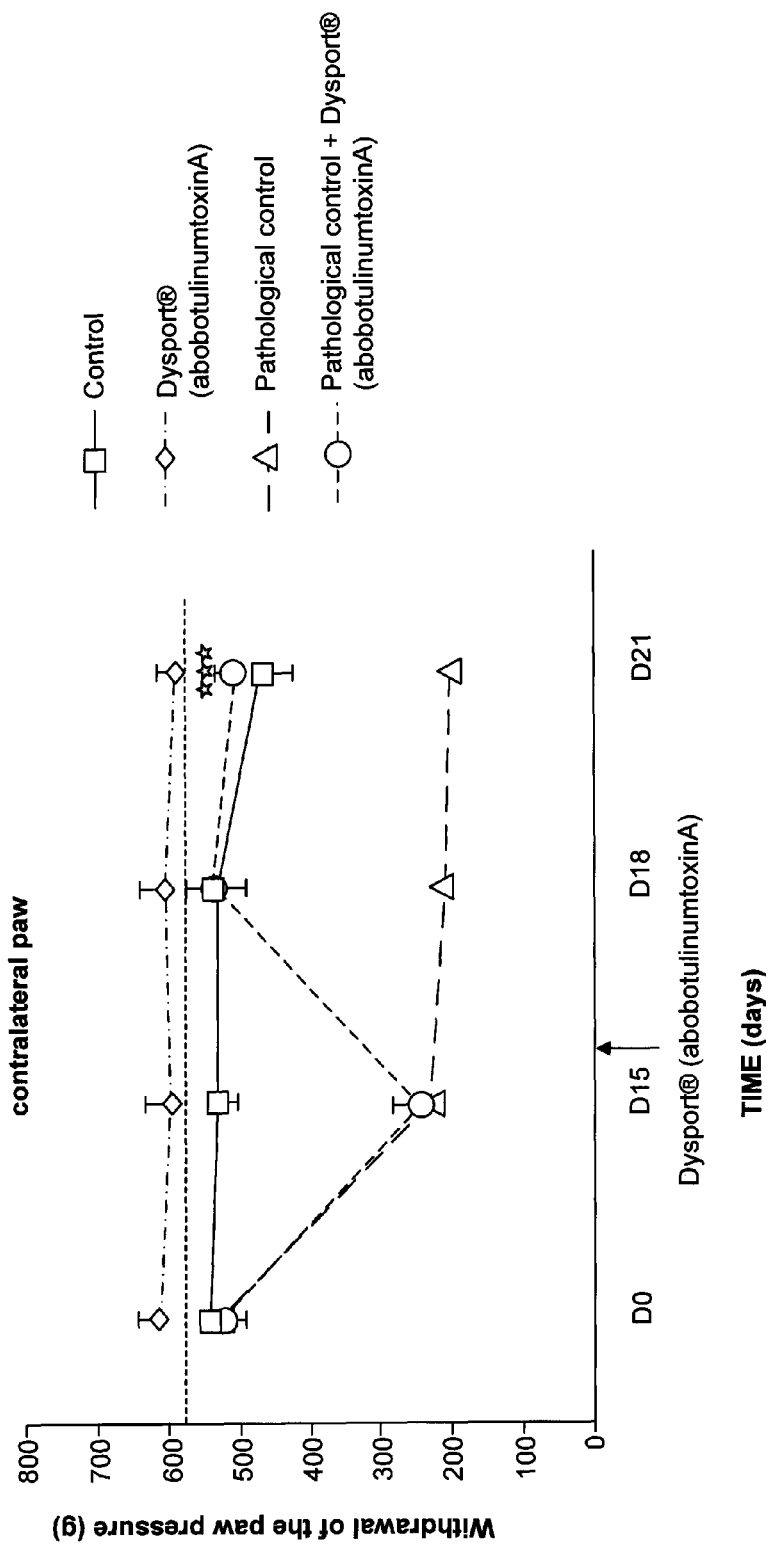
FIG. 2 shows the effect of botulinum toxin type A1 on the left paw (contralateral) following the injection by subplantar route into the right paw (ipsilateral) in the model of peripheral neuropathy induced by paclitaxel.
Figure 3:
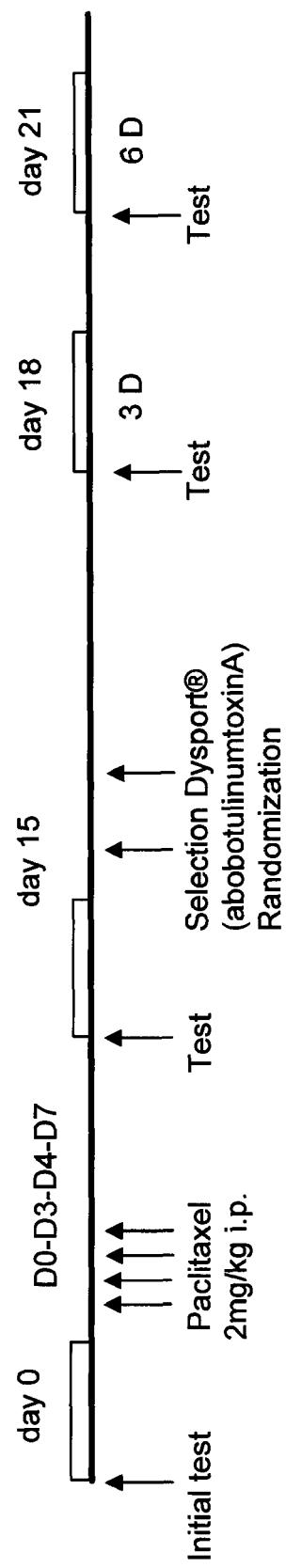
FIG. 3 shows the injection protocol.

FIG. 2 shows the effect of Dysport (abobotulinumtoxinA) on the left paw (contralateral) following the injection by subplantar route into the right paw (ipsilateral) in The control indicates the pain threshold tolerated by the rat when increasing pressure is applied to its paws; this group was treated with the paclitaxel vehicle (3% MONTANOX® (polysorbate 80) in 0.9% NaCl) by intra-peritoneal route and with the Dysport® (abobotulinumtoxinA) vehicle (0.9% NaCl) subplantar. From D0 to D21, the nociception threshold is approximately 500 g/mm$^2$.

The pathological control indicates the pain threshold tolerated by the rat when increasing pressure is applied to its paws; this group was treated with paclitaxel by intra-peritoneal route and with the Dysport® (abobotulinumtoxinA) vehicle (0.9% NaCl) subplantar. On day zero this threshold is approximately 536 g/mm$^2$, then decreases reaching approximately 228 g/mm$^2$ on day 15, 216 mm$^2$ on day 18 and 204 g/mm$^2$ on day 21. These results indicate that after i.p. injection of paclitaxel, the sensitivity of the paws of the rats is increased following the application of pressure on them.

The administration of Dysport® (abobotulinumtoxinA) at a dose of 20 U/kg subplantar in a group treated only with the paclitaxel vehicle (3% MONTANOX® (polysorbate 80) in NaCl 0.9%) by intra-peritoneal route, indicates that the pain threshold tolerated by the rat is not significantly modified. The pain threshold following a mechanical stimulus applied to the paws of the rats is approximately 610 g/mm$^2$ from D0 to D21.

The administration of Dysport® (abobotulinumtoxinA) at a dose of 20 U/kg subplantar into the right paw in a group treated with paclitaxel indicates that the pain threshold tolerated by the rat on its left paw increases. The pain threshold following a mechanical stimulus applied to the paws of the rats is significantly increased, reaching approximately 540 g/mm$^2$ on D18 (i.e., 3 days after the treatment with Dysport® (abobotulinumtoxinA)) and 512 g/mm$^2$ on D21 (i.e. 6 days after the treatment with Dysport® (abobotulinumtoxinA)) compared with 244 g/mm$^2$ on D15 (before Dysport® (abobotulinumtoxinA)).

These results indicate that the administration of Dysport® (abobotulinumtoxinA) subplantar in the right paw of the rats induces an analgesic effect, measured on the two rear paws of the rats, in this test of peripheral neuropathy induced by four consecutive and systemic injections of paclitaxel.

The invention claimed is:

1. A method of treating post-chemotherapy pain or pains in a patient in need thereof, comprising the step of administering by an intramuscular, intradermal, or subcutaneous route at least one botulinum neurotoxin at a dose between 0.01 to 1500 U, thereby providing systemic effect against the post-chemotherapy pain or pains.

2. The method of claim 1, wherein said post-chemotherapy pain or pains are induced by an anti-neoplastic agent or a salt thereof.

3. The method of claim 2, wherein said anti-neoplastic agent or salt thereof is a taxane, a platinum salt, or any combination thereof.

4. The method of claim 2, wherein said anti-neoplastic agent or salt thereof is docetaxel, paclitaxel, or any combination thereof.

5. The method of claim 3, wherein said anti-neoplastic agent or salt thereof is cisplatin, oxaliplatin, carboplatin, or any combination thereof.

6. The method of claim 2, wherein said anti-neoplastic agent or salt thereof is vincristine, vinblastine, etoposide, teniposide, Ara-A (adenoside-arabinoside), Ara-C (cytarabine), fluorouracil, procarbazine, vinorelbine, gemcitabine, or a mixture of paclitaxel and carboplatin, paclitaxel and an anthracycline, paclitaxel, carboplatin, and gemcitabine, paclitaxel and estramustine, docetaxel and cisplatin, docetaxel and doxorubicin, docetaxel and vinorelbine, docetaxel and trastuzumab, docetaxel and capecitabine, cisplatin and cyclophosphamide, cisplatin and irinotecan, carboplatin and topotecan, carboplatin and estramustine, etoposide and estramustine, or vinblastine and estramustine.

7. The method of claim 1, wherein said botulinum neurotoxin is of type A, A1, A2, B, C, C1, D, E, F or G.

8. The method of claim 7, wherein said botulinum neurotoxin is of type A1.

9. The method of claim 1, further comprising combining said botulinum neurotoxin with at least one polysaccharide.

10. The method of claim 9, wherein said at least one polysaccharide is 2-hydroxy-ethyl starch.

11. The method of claim 1, wherein said botulinum neurotoxin is a modified botulinum neurotoxin comprising at least one deleted, modified or replaced amino acid.

12. The method of claim 1, further comprising combining said botulinum neurotoxin with at least one surfactant.

13. The method of claim 12, wherein the at least one surfactant is a cationic, anionic, or non-ionic surfactant.

14. The method of claim 12, wherein the at least one surfactant is non-ionic and a polysorbate.

15. The method of claim 1, wherein said patient experiences post-chemotherapy pain or pains resulting from the treatment of cancers of the colon, rectum, breast, lungs, pancreas, testicles, kidney, uterus, ovary, prostate, skin, bones, or spinal cord or sarcomas, carcinomas, fibroadenomas, neuroblastomas, leukaemias, lymphomas, or melanomas.

16. A method of treating post-chemotherapy pain or pains in a patient in need thereof comprising the step of administering by an intramuscular, intradermal, or subcutaneous route at least one botulinum neurotoxin at a dose of 20 U/kg, thereby providing systemic effect against the post-chemotherapy pain or pains within 3 days from botulinum toxin injection.

* * * * *